United States Patent
Chandrasekaran

[11] Patent Number: 6,093,157
[45] Date of Patent: *Jul. 25, 2000

[54] RADIOPAQUE GUIDE WIRE

[75] Inventor: Verivada C. Chandrasekaran, Mercer Island, Wash.

[73] Assignee: SCIMED Life Systems, Inc., Maple Grove, Tenn.

[*] Notice: This patent issued on a continued prosecution application filed under 37 CFR 1.53(d), and is subject to the twenty year patent term provisions of 35 U.S.C. 154(a)(2).

[21] Appl. No.: 08/956,147

[22] Filed: Oct. 22, 1997

[51] Int. Cl.$^7$ .......................................... A61B 5/00

[52] U.S. Cl. .......................................... 600/585

[58] Field of Search .............................. 606/159; 604/22, 604/96, 282, 164; 600/585

[56] References Cited

U.S. PATENT DOCUMENTS

| | | |
|---|---|---|
| 4,168,214 | 9/1979 | Fletcher et al. . |
| 4,282,876 | 8/1981 | Flynn .................................. 128/349 R |
| 4,345,602 | 8/1982 | Yoshimura et al. ................ 128/349 R |

(List continued on next page.)

FOREIGN PATENT DOCUMENTS

| | | |
|---|---|---|
| 0 340 304 A1 | 11/1989 | European Pat. Off. . |
| 0 380 102 A1 | 8/1990 | European Pat. Off. . |
| 0 395 098 A1 | 10/1990 | European Pat. Off. . |
| 0 405 823 A2 | 1/1991 | European Pat. Off. . |
| 0 407 965 A1 | 1/1991 | European Pat. Off. . |
| 0 480 667 B1 | 3/1996 | European Pat. Off. . |
| 0 709 068 A2 | 5/1996 | European Pat. Off. . |
| 0 380 668 B1 | 12/1996 | European Pat. Off. . |
| 0 836 839 A2 | 4/1998 | European Pat. Off. . |
| 2 401 668 | 8/1977 | France . |
| 60-12069 | 1/1985 | Japan . |
| 2-180277 | 7/1990 | Japan . |
| 8-257133 | 1/1996 | Japan . |
| 2 076 427 | 12/1981 | United Kingdom . |
| WO 85/01444 | 4/1985 | WIPO . |
| WO 89/09626 | 10/1989 | WIPO . |
| WO 91/00051 | 1/1991 | WIPO . |

OTHER PUBLICATIONS

Tegtmeyer, "Current Problems in Diagnostic Radiology", vol. XVI, No. 2, Mar./Apr., 1987, pp. 79–80.

Rogers, J.A. et al., "Microcontact Printing and Electroplating on Curved Substrates: Production of Free–Standing Three–Dimensional Metallic Microstructures", *Adv. Mater.* vol. 9, No. 6, pp. 475–477, 1997.

Yachia, D. and Aridogan, I.A., "Comparison between First–Generation (Fixed Caliber) and Second–Generation (Self–Expanding, Large Caliber) Temporary Prostatic Stents", *Urol Int*, vol. 57, pp. 165–169, 1997.

Hehrlein, C. et al., "Influence of surface texture and charge on the biocompatibility of endovascular stents", *Coronary Artery Disease*, vol. 6, No. 7, pp. 581–586, Jul. 1995.

(List continued on next page.)

*Primary Examiner*—Michael Buiz
*Assistant Examiner*—Kevin Truong
*Attorney, Agent, or Firm*—Christensen O'Connor Johnson & Kindness PLLC

[57] ABSTRACT

A guide wire including a radiopaque distal region having a wear resistant surface suitable for carrying the rotating drive shaft of an atherectomy device. One guide wire is formed of a stainless steel shaft having a radiopaque layer over the distal region, the radiopaque layer including a harder gold alloy over softer gold or a gold alloy layer. The harder gold alloy provides a harder, less flexible, wear resistant surface while the softer gold layer provides a softer, more flexible, less wear resistant surface. Limiting the thickness of a harder gold alloy layer can limit problems caused by flexing the distal region and problems increased by residual stresses existing within the layer. One distal radiopaque layer includes alternating layers of harder and softer gold alloys. Another distal radiopaque layer increases flexibility by having longitudinally discontinuous harder gold alloy bands, such as rings or a helical spiral. Another guide wire includes a distal hypotube segment, with an external radiopaque layer or an internal radiopaque material within the tube.

9 Claims, 1 Drawing Sheet

U.S. PATENT DOCUMENTS

| | | | |
|---|---|---|---|
| 4,422,906 | 12/1983 | Kobayashi . | |
| 4,456,017 | 6/1984 | Miles | 128/772 |
| 4,534,363 | 8/1985 | Gold | 128/772 |
| 4,537,663 | 8/1985 | Macdonald . | |
| 4,642,267 | 2/1987 | Creasy et al. | 428/413 |
| 4,682,607 | 7/1987 | Vaillancourt et al. | 128/772 |
| 4,721,117 | 1/1988 | Mar et al. | 128/772 |
| 4,729,914 | 3/1988 | Kliment et al. | 428/36 |
| 4,739,768 | 4/1988 | Engelson | 128/658 |
| 4,811,743 | 3/1989 | Stevens | 128/772 |
| 4,835,003 | 5/1989 | Becker et al. | 427/2 |
| 4,867,174 | 9/1989 | Skiribiski | 128/772 |
| 4,884,579 | 12/1989 | Engelson | 128/772 |
| 4,899,787 | 2/1990 | Ouchi et al. | 138/131 |
| 4,922,924 | 5/1990 | Gambale et al. | 128/772 |
| 4,925,445 | 5/1990 | Sakamoto et al. | 604/95 |
| 4,955,862 | 9/1990 | Sepetka | 604/164 |
| 4,961,731 | 10/1990 | Bodicky et al. | 604/264 |
| 4,977,901 | 12/1990 | Ofstead | 128/772 |
| 4,991,602 | 2/1991 | Amplatz et al. | 128/772 |
| 5,045,072 | 9/1991 | Castillo et al. | 604/280 |
| 5,061,254 | 10/1991 | Karakelle et al. | 604/265 |
| 5,069,226 | 12/1991 | Yamauchi et al. | 128/772 |
| 5,078,702 | 1/1992 | Pomeranz | 604/280 |
| 5,095,915 | 3/1992 | Engelson | 128/772 |
| 5,129,890 | 7/1992 | Bates et al. | 604/281 |
| 5,144,959 | 9/1992 | Gambale et al. | 128/772 |
| 5,176,149 | 1/1993 | Grenouillet | 128/772 |
| 5,217,026 | 6/1993 | Stoy et al. | 128/772 |
| 5,253,653 | 10/1993 | Daigle et al. | 128/772 |
| 5,333,620 | 8/1994 | Moutafis et al. | 128/772 |
| 5,365,943 | 11/1994 | Jansen | 128/772 |
| 5,379,779 | 1/1995 | Rowland et al. | 128/772 |
| 5,384,026 | 1/1995 | McLaughlin . | |
| 5,409,015 | 4/1995 | Palermo | 128/772 |
| 5,411,476 | 5/1995 | Abrams et al. | 604/95 |
| 5,421,349 | 6/1995 | Rodriguez et al. | 128/772 |
| 5,437,288 | 8/1995 | Schwartz et al. | 128/772 |
| 5,452,726 | 9/1995 | Burmeister et al. | 128/772 |
| 5,497,783 | 3/1996 | Urick et al. | 128/772 |
| 5,507,301 | 4/1996 | Wasicek et al. | 128/772 |
| 5,533,985 | 7/1996 | Wang | 604/264 |
| 5,607,442 | 3/1997 | Fischell et al. . | |
| 5,630,806 | 5/1997 | Inagaki et al. | 604/282 |
| 5,637,089 | 6/1997 | Abrams et al. | 604/95 |
| 5,664,580 | 9/1997 | Erickson et al. | 600/585 |
| 5,724,989 | 3/1998 | Dobson | 604/96 |
| 5,824,045 | 10/1998 | Alt . | |

OTHER PUBLICATIONS

Tanigawa, N. et al., "Reaction of the Aortic Wall to Siz Metallic Stent Materials", *Acad Radiol*, vol. 2, pp. 379–384, 1995.

Isogawa, Y. and Ohmori, K., "Application of Urethral Stent Under Metal Bougie Guidance", *Acta Urol Jpn*, vol. 39, pp. 231–235, 1995. Translation Not Provided.

RADIOPAQUE GUIDE WIRE

FIELD OF THE INVENTION

The present invention relates generally to medical, intravascular guide wires. Specifically, the present invention relates to a radiopaque coating for guide wires used to guide atherectomy devices.

BACKGROUND OF THE INVENTION

Vascular diseases, such as atherosclerosis and the like, have become quite prevalent in the modern day. These diseases may manifest themselves in a number of ways, often requiring different forms or methods of treatment for curing the adverse effects of the diseases. Vascular diseases, for example, may take the form of deposits or growths in a patient's vasculature which may restrict, in the case of a partial occlusion, or, stop, in the case of a total occlusion, blood flow to a certain portion of the patient's body. This can be particularly serious if, for example, such an occlusion occurs in a portion of the vasculature that supplies vital organs with blood or other necessary fluids.

To treat these diseases, a number of different therapies have been developed. While a number of effective invasive therapies are available, it is desired to develop non-invasive therapies as well. Non-invasive therapies may be more desirable because of the possibility of decreased chances of infection, reduced post-operative pain, and less post-operative rehabilitation. Drug therapy is one type of non-invasive therapy developed for treating vascular diseases. Clot-busting drugs have been employed to help break up blood clots which may be blocking a particular vascular lumen. Other drug therapies are also available. Further non-invasive intravascular treatments exist that are not only pharmaceutical, but also physically revascularize lumens. Two examples of such intravascular therapies are balloon angioplasty and atherectomy, both of which physically revascularize a portion of a patient's vasculature.

Balloon angioplasty is a procedure wherein a balloon catheter is inserted intravascularly into a patient through a relatively small puncture, which may be located proximate the groin, and intravascularly navigated by a treating physician to the occluded vascular site. The balloon catheter includes a balloon or dilating member which is placed adjacent the vascular occlusion and is then inflated. Intravascular inflation of the dilating member by sufficient pressures, on the order of 5 to 12 atmospheres or so, causes the balloon to displace the occluding matter to revascularize the occluded lumen and thereby restore substantially normal blood flow through the revascularized portion of the vasculature. It is to be noted, however, that this procedure does not remove that matter from the patient's vasculature, but displaces and reforms it.

While balloon angioplasty is quite successful in substantially revascularizing many vascular lumens by reforming the occluding material, other occlusions may be difficult to treat with angioplasty. Specifically, some intravascular occlusions may be composed of an irregular, loose or heavily calcified material which may extend relatively far along a vessel or may extend adjacent a side branching vessel, and thus may not be prone or susceptible to angioplastic treatment. Even if angioplasty is successful, there is a chance that the occlusion may recur. Recurrence of an occlusion may require repeated or alternative treatments given at the same intravascular site.

Accordingly, attempts have been made to develop other alternative mechanical methods of non-invasive, intravascular treatment in an effort to provide another way of revascularizing an occluded vessel and of restoring blood flow through the relevant vasculature. These alternative treatments may have particular utility with certain vascular occlusions, or may provide added benefits to a patient when combined with balloon angioplasty or drug therapies.

One such alternative mechanical treatment method involves removal, not displacement of the material occluding a vascular lumen. Such treatment devices, sometimes referred to as atherectomy devices, use a variety of material removal means, such as rotating cutters or ablaters for example, to remove the occluding material. The material removal device is typically rotated via a drive shaft that extends out of the vascular of the patient and to an electric motor or the like.

In operation, an atherectomy device is typically advanced over a guide wire that is placed in-vivo until the material removal device is positioned just proximal to the occluded site. The motor is then used to rotate both the drive shaft and the material removal device, while the material removal device is moved through the occluded vessel. The material removal device typically ablates the material from the vessel, rather than merely displacing or reforming the material as in a balloon angioplasty procedure.

The guide wire used is subject to greater wear than guide wires used for advancing many other catheters, as the rotating drive shaft is often advanced directly over the guide wire. A stainless steel guide wire is often used, as the surface is sufficiently hard to withstand the wear of the rotating drive shaft. Stainless steel is not sufficiently radiopaque to render the guide wire visible under fluoroscopy however. The guide wire commonly has a distal outer diameter of about 6 thousandths of an inch, and the options for making the narrow wire radiopaque are limited. Gold is radiopaque, but can be too soft to withstand the wear of the rotating drive shaft. Gold can be alloyed, making it harder, but a harder layer over the guide wire can include residual, inner stresses created during manufacture and can also prove too brittle to stand up to repeated flexure through the vasculature.

It would be desirable, therefore, to provide a guide wire that is visible under fluoroscopy, can stand up to the demands of guiding a rotating atherectomy device, and is not likely to develop cracks caused by bending or residual stress. What would be desirable and has not hitherto been provided is a radiopaque guide wire having a harder surface with more flexibility and less residual stress.

SUMMARY OF THE INVENTION

The present invention provides a guide wire including a radiopaque distal portion having a wear resistant surface suitable for carrying the rotating drive shaft of an atherectomy device. A preferred guide wire has an outside diameter of about 0.006 inches and a radiopaque layer about 300 microinches thick. One radiopaque layer includes a harder, less flexible gold alloy disposed over a softer, more flexible gold or gold alloy. Suitable alloying additives include cobalt. Gold provides both radiopacity and lubricity to the distal guide wire region. Another embodiment radiopaque layer includes a harder layer disposed over a softer layer disposed over a harder layer disposed over a softer layer. Limiting the thickness of the harder, less flexible layers provides increased flexibility and reduces problems such as cracking within the harder layer, which can occur when flexing the distal portion, and which can be more pronounced in thicker, harder gold alloy layers. An alternate embodiment radiopaque layer includes a substantially continuously varying alloy composition and hardness, increasing in hardness with increasing radial distance from the guide wire shaft.

Another guide wire distal radiopaque layer achieves increased flexibility with longitudinally discontinuous bands of harder gold alloy material, including a series of circular rings about the guide wire or a helical spiral about the guide wire. The bands are preferably separated by a distance sufficiently small to present a continuous radiopaque image under fluoroscopy. In embodiments having a spiral band or discrete rings, the problems due to residual stress and flexure of the guide wire are reduced by limiting the longitudinal dimension of the harder alloy layer.

Yet another guide wire includes a distal hypotube segment providing a stainless steel distal portion having good wear resistance. The hypotube segment can have a radiopaque layer thereover as previously discussed. In one embodiment, the guide wire includes radiopaque material within the hypotube lumen. Preferred radiopaque materials within the hypotube lumen include gold and platinum, and tungsten and biocompatible alloys of these high density metals.

The present invention thus provides a guide wire having a flexible, wearable, and radiopaque distal region. The guide wire distal region presents both an external surface suitable for carrying a rotating atherectomy drive shaft and for presenting a radiopaque image under fluoroscopy.

DETAILED DESCRIPTION OF THE PREFERRED EMBODIMENTS

Figure 1:
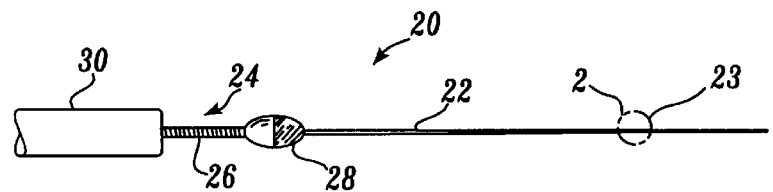
FIG. 1 is a fragmentary side view of an atherectomy device within a guide catheter disposed over a guide wire.

FIG. 1 illustrates an atherectomy system 20 including a guide catheter 30 having an atherectomy device 24 disposed within and a guide wire 22 disposed within atherectomy device 24. Atherectomy device 24 includes a drive shaft 26 operably connected proximally to a drive motor and connected distally to a cutting or abrasive head or burr 28. Drive shaft 26 includes a lumen which can slidably receive guide wire 22. Guide wire 22 has a distal region 23.

Figure 2:
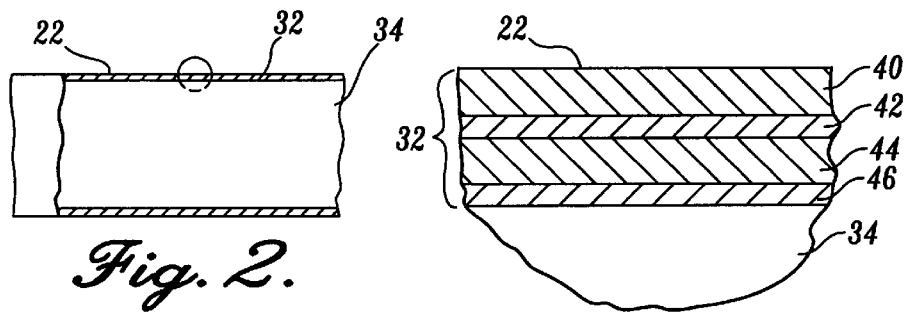
FIG. 2 is an enlarged, side, cross-sectional view of guide wire detail area 2 of FIG. 1.

Referring now to FIG. 2, detail area 2 of guide wire 22 in FIG. 1 is illustrated in more detail. Guide wire 22 includes generally a shaft 34 and a radiopaque layer 32. Shaft 34 is preferably solid and can be formed of stainless steel such as high strength Hyten 304V stainless steel. Shaft 34 can also be formed of superelastic materials such as Nitinol or cobalt base alloys such as Elgiloy. A preferred diameter for guide wires according to the present invention is about 0.005 to about 0.008 inches. Radiopaque layer 32 is preferably about 150–300 microinches thick. One embodiment layer is about 300 microinches thick. Proximal to the radiopaque segment of the guide wire, the remaining wire length can be plated with a thin gold layer. The gold layer in one embodiment is about 50–100 microinches thick and can reduce friction between guide wire and rotating atherectomy device.

Figures 3, 4, 5:
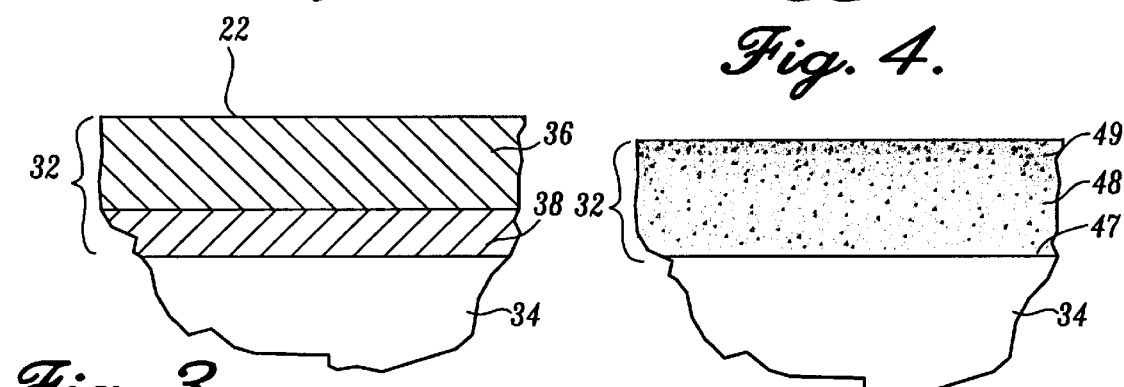
FIG. 3 is an enlarged, side, cross-sectional view of detail area A of FIG. 2 in a guide wire having a harder and a softer layer.
FIG. 4 is an enlarged, side, cross-sectional view of detail area A of FIG. 2 in a guide wire having 2 harder and 2 softer layers.
FIG. 5 is an enlarged, side, cross-sectional view of detail area A of FIG. 2 in a guide wire having radially varying hardness.

Referring now to FIG. 3, a preferred embodiment of radiopaque layer 32 is illustrated. Radiopaque layer 32, in this embodiment, includes an outer, harder, radiopaque layer 36 over an inner, softer, radiopaque layer 38. Softer layer 38 is preferably formed of gold. Harder radiopaque layer 36 is preferably formed of a harder gold alloy, such as an alloy containing cobalt. Harder layer 36 and softer layer 38 can be deposited using electroplating or another method such as sputtering and ion beam assisted deposition. While gold is a preferred radiopaque material having desirable wear resistance, platinum is radiopaque material also within the scope of the invention. Radiopaque layer 32 preferably has a total thickness of about 300 microinches and a length of about 5 inches. Harder layer 36 preferably has a thickness of about 200 microinches while softer layer 38 preferably has a thickness of about 100 microinches.

Having harder layer 36 over softer layer 38 provides a protective, wear resistant layer over the softer layer below. Harder layer 36 may be necessary to protect softer layer 38 from the wear of a rotating atherectomy drive shaft disposed over the guide wire. While harder layer 36 can serve to protect softer layer 38, the harder gold alloy is harder and less flexible than soft layer 38 below. The hardness is a desirable attribute while the lesser flexibility is not, as the guide wire may be required to traverse tortuous paths through the vasculature. A harder layer over a flexing guide wire is more prone to cracking under stress than a softer layer. A thicker, harder layer can have residual stress within, which is disrupted and mitigated by interrupting the thicker layer with softer layers. Residual stresses are inner stresses, existing within a layer even when no external stresses are present, formed by a manufacturing process such as plating. Residual stresses are deviations from perfection which can add to stresses caused by flexing the guide wire. The combined internal and external stresses can compromise the integrity of the harder gold layer. The reduced flexibility and increased residual stresses within the harder layer can be partially alleviated by making the harder layer thinner, and using a softer gold alloy below which is less wear resistant but is more flexible. Making the harder layer thinner by using a softer layer for part of the radiopaque layer thickness provides the benefits of radiopacity, wear resistance, and flexibility.

Referring now to FIG. 4, another embodiment is illustrated, having a softer layer 46 over guide wire shaft 34, a harder layer 44 over softer layer 46, a softer layer 42 over harder layer 44, and an outer, harder layer 40 over softer layer 42. Harder layers 40 and 44 preferably each have a thickness of about 100 microinches while softer layers 42 and 46 preferably each have a thickness of about 50 microinches. Providing alternating hard and soft layers allows use of even thinner harder layers, providing increased flexibility and less residual stress within the harder layer.

Referring now to FIG. 5, an alternate embodiment of radiopaque layer 32 is illustrated. Radiopaque layer 32 is formed of a substantially continuously variable composition layer 48, with layer 48 preferably being softest where meeting guide wire shaft 34 at 47, and hardest near the surface at 49. The alloy composition of layer 48 can be varied utilizing vacuum deposition chambers equipped with energetic sputtering or ion beam assisted processes. The composition of the gold alloy can vary with increasing thickness, providing the benefits of a hard external wear surface and a graded, more flexible underlying layer having less residual stress.

Figure 6:
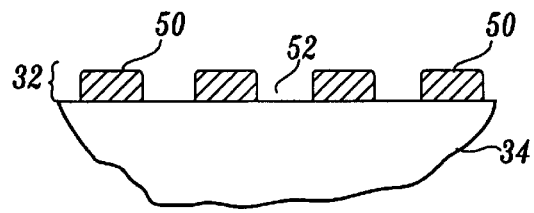
FIG. 6 is an enlarged, side, cross-sectional view of detail area A of FIG. 2 in a guide wire having a longitudinally discontinuous layer.

Referring now to FIG. 6, another embodiment of radiopaque layer 32 is illustrated. A series of longitudinally discontinuous bands or stripes 50 separated by inter-band regions 52 provides another structure for providing less residual stress and greater flexibility in a wear resistant radiopaque layer. While the embodiments of FIGS. 3 and 4 increase flexibility by reducing the radial thickness of the harder layers, the embodiment of FIG. 6 achieves these results by reducing the longitudinal dimension of the harder layer. In one embodiment, bands 50 form a series of circular bands about the circumference of the guide wire. In another embodiment, bands 50 are part of a substantially continuous helical spiral about the guide wire. The longitudinal width of the bands in a preferred embodiment is about 1 cm, and the preferred inter-band region width is less than or equal to 1 cm. A preferred radiopaque layer utilizes a harder gold alloy for construction of bands 50. An alternate embodiment utilizes layers as discussed with respect to FIG. 3 and 4. In a preferred embodiment, distinct bands 50 are not visible under fluoroscopy, but appear continuous. Bands 50 provide increased wear resistance and increased flexibility over a solid, continuous harder layer.

Figure 7:
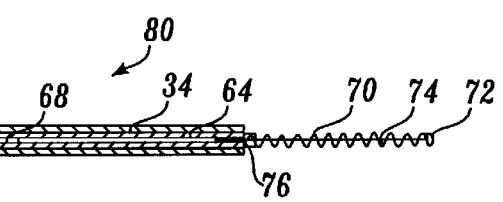
FIG. 7 is a side, cross-sectional view of a guide wire including a distal hypotube having gold plating thereover and a lumen within.

Referring now to FIG. 7, another embodiment guide wire 80 is illustrated. Guide wire 80 includes a stainless steel tube 64, preferably formed of hypotube. Guide wire 80 includes a guide wire shaft 60 having a distal shoulder 62 bonded at 66 to tube 64. Tube 64 is bonded to a distal wire segment 74 at 76, with distal wire segment 74 having a helical coil 70 disposed about the segment and a distal tip 72 formed at the distal end. Bonds 66 and 76 can be formed using solder. Distal wire segment 74 and distal coil 70 are preferably formed of stainless steel and a radiopaque material such as a platinum alloy. Distal coil 70 provides a flexible distal tip that is able to bend sufficiently to travel through tortuous vessel passages. Distal tube 64 is preferably hollow, having a lumen 68 within. Distal tube 64 has radiopaque layer 34 thereover, discussed with respect to FIGS. 3 through 6 above. Distal tube 64 can provide a limited length stainless steel segment, allowing use of a guide wire formed of a different material proximally. Where distal tube 64 is formed of hypotube, tube 64 provides a wear resistant stainless steel tube having the radiopaque layer discussed previously.

Figure 8:
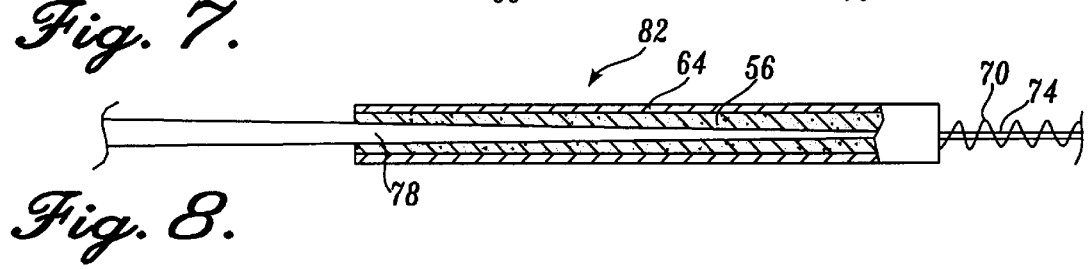
FIG. 8 is a side, cross-sectional view of a guide wire including a distal hypotube having the guide wire shaft and a radiopaque substance disposed within the hypotube.

Referring now to FIG. 8, another guide wire 82 with a guide wire shaft 78 and distal tube 64 is illustrated. Guide wire shaft 78 extends through distal tube 64, and can terminate within the distal end of tube 64. Included within tube 64 is a radiopaque material 56. In a preferred embodiment, radiopaque material 56 includes gold or platinum. Other embodiments include tungsten. Guide wire 82 also includes distal wire segment 74 and coil 70, discussed with respect to FIG. 7. Guide wire 80 provides a stainless steel tube 64 having good wear characteristics for carrying a rotating atherectomy drive shaft, while providing radiopaque material 56 within tube 64.

Figure 9:
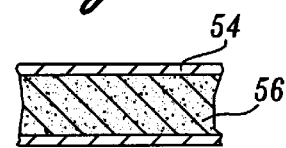
FIG. 9 is a fragmentary, side, cross-sectional view of a hypotube containing a radiopaque substance, suitable for inclusion in a guide wire such as the guide wire of FIG. 7.

Referring now to FIG. 9, an alternate embodiment distal tube 54 is illustrated, containing radiopaque material 56 within. Distal tube 54 is suitable for inclusion in a guide wire such as guide wire 80 in FIG. 7. Where guide wire 80 has radiopaque material disposed about distal tube 34 as layer 34, tube 54 contains radiopaque material 56 within. Radiopaque material 56 can be contained within a lumen such as lumen 68 inside distal tube 64.

Numerous advantages of the invention covered by this document have been set forth in the foregoing description. It will be understood, however, that this disclosure is, in many respects, only illustrative. Changes may be made in details, particularly in matters of shape, size, and arrangement of parts without exceeding the scope of the invention. The inventions's scope is, of course, defined in the language in which the appended claims are expressed.

What is claimed is:

1. An intravascular guide wire comprising:
   an elongate shaft having a distal region;
   a radiopaque layer over said shaft distal region, said radiopaque layer including a softer inner layer and an outer layer coated over the inner layer and having a hardness that is harder than the hardness of the soft inner layer.

2. An intravascular guide wire as recited in claim 1, wherein said soft inner layer includes gold and said outer layer includes a gold alloy having a hardness greater than the hardness of pure gold.

3. An intravascular guide wire comprising:
   an elongate shaft having a distal region,
   a radiopaque layer over said shaft distal region, said radiopaque layer including a first, softer, inner layer including gold and a second, harder, outer layer of a gold alloy having a hardness greater than the hardness of pure gold.

4. An intravascular guide wire as recited in claim 3, wherein said radiopaque layer includes a first, softer, inner layer, a second, harder layer over said first layer, a third, softer layer over said second layer, and a fourth, harder layer over said third layer, wherein said harder layers are harder than said softer layers.

5. An intravascular guide wire as recited in claim 4, wherein said first layer is about 50 microinches in thickness, said second layer is about 100 microinches in thickness, said third layer is about 50 microinches in thickness and said fourth layer is about 100 microinches in thickness.

6. An atherectomy system comprising:
   an intravascular guide wire including an elongate shaft having a distal region and a radiopaque layer over said shaft distal region, said radiopaque layer including a first softer inner layer including gold and a second, harder outer layer including a gold alloy having a hardness greater than the hardness of pure gold; and
   an atherectomy device including
     a rotatable drive shaft having distal end and a lumen therethrough adapted to receive said guide wire, and
     a rotatable cutting head disposed at said drive shaft distal end, said cutting head being driven by said drive shaft.

7. An atherectomy system as recited in claim 6, wherein said radiopaque layer includes a first, softer layer, a second, harder layer over said first layer, a third, softer layer over said second layer, and a fourth, harder layer over said third layer.

8. An atherectomy system as recited in claim 7, wherein said first layer is about 50 microinches in thickness, said second layer is about 100 microinches in thickness, said third layer is about 50 microinches in thickness and said fourth layer is about 100 microinches in thickness.

9. A method for performing atherectomy at a blockage within a vessel comprising:

providing an intravascular guide wire including an elongate shaft having a distal region having an outer surface, a radiopaque layer over said shaft distal region, said radiopaque layer including gold and having a harder gold alloy at said outer surface, said harder gold alloy having a hardness greater than the hardness of pure gold;

providing an atherectomy device including a rotatable drive shaft operably coupled to a cutting head;

advancing said guide wire into said vessel near said blockage;

advancing said atherectomy device over said guide wire to said blockage; and rotating said atherectomy device over said guide wire and against said blockage, such that said blockage is reduced in size.

* * * * *